（12）United States Patent
Luecke et al.

(10) Patent No.: US 8,130,900 B2
(45) Date of Patent: Mar. 6, 2012

(54) COMPUTED TOMOGRAPHY GANTRY ROTOR

(75) Inventors: Daniela Luecke, Germering (DE); Hans-Juergen Mueller, Pretzfeld (DE)

(73) Assignee: Siemens Aktiengesellschaft, Munich (DE)

( * ) Notice: Subject to any disclaimer, the term of this patent is extended or adjusted under 35 U.S.C. 154(b) by 210 days.

(21) Appl. No.: 12/533,148

(22) Filed: Jul. 31, 2009

(65) Prior Publication Data

US 2010/0025590 A1 Feb. 4, 2010

(30) Foreign Application Priority Data

Aug. 1, 2008 (DE) .......................... 10 2008 036 015

(51) Int. Cl.
*H05G 1/60* (2006.01)
(52) U.S. Cl. ......................................................... 378/15
(58) Field of Classification Search ................ 378/4, 19, 378/15, 193, 196, 197
See application file for complete search history.

(56) References Cited

U.S. PATENT DOCUMENTS

| 7,188,998 | B2 * | 3/2007 | Gregerson et al. ............ 378/197 |
| 2006/0018437 | A1 | 1/2006 | Russinger |
| 2007/0064863 | A1 | 3/2007 | Buttner et al. |

FOREIGN PATENT DOCUMENTS

| DE | 42 14 858 C1 | 2/1994 |
| DE | 20 2006 004 118 U1 | 8/2007 |

OTHER PUBLICATIONS

U.S. Appl. No. 12/533,213, filed Jul. 31, 2009.
U.S. Appl. No. 12/533,198, filed Jul. 31, 2009.
U.S. Appl. No. 12/533,184, filed Jul. 31, 2009.
U.S. Appl. No. 12/533,228, filed Jul. 31, 2009.

* cited by examiner

*Primary Examiner* — Irakli Kiknadze
(74) *Attorney, Agent, or Firm* — Schiff Hardin LLP

(57) ABSTRACT

A rotor of a gantry of a computed tomography apparatus is produced at least in sections in a differential style from bar-shaped basic elements. Due to the differential style of the rotor, the rotation mass is reduced to a significant degree given a simultaneously maintained rigidity and stability of the rotor 1, such that high rotation speeds can be realized with a comparably small dimensioning of the rotor drive.

17 Claims, 2 Drawing Sheets

COMPUTED TOMOGRAPHY GANTRY ROTOR

BACKGROUND OF THE INVENTION

1. Field of the Invention

The invention concerns a rotor for a gantry of a computed tomography apparatus and a computed tomography apparatus with such a rotor.

2. Description of the Prior Art

Computed tomography apparatuses enable the reconstruction of three-dimensional slice or volume images of an examination region for diagnostic purposes. The reconstruction of an image ensues on the basis of projections of an examination region that are acquired by irradiating a subject with an x-ray fan beam from different projection directions by rotation of an acquisition device, so that measurement data for parallel projections from an angle range of at least 180 degrees plus the fan beam angle are obtained for reconstruction of an image. To produce the rotation of the acquisition device, the computed tomography apparatus has a gantry that has a stationary rotating frame and a rotor mounted so that it can rotate by means of a rotating support device. The acquisition device is mounted on this rotor. The rotor has conventionally been fabricated as a cast part made of an aluminum alloy AlZn10SiMg with a rotor wall in the form of an annular disc and a retention ring running along its outer periphery for mounting the components of the acquisition device. The wall thicknesses of the rotor vary between 15 and 20 mm.

To avoid movement artifacts in the reconstructed image that can arise due to patient or organ movements, it is sought to select the time window for acquisition of the projections required for reconstruction to be as small as possible by the use of high rotation speeds. Rotation speeds of 210 R/min are achieved in current computed tomography apparatuses. However, in the future the rotation speeds should be raised to at least 300 R/min.

Due to a combination of high rotation speed, large rotation radius and high rotation mass, the rotor represents a highly mechanically stressed component that, in addition to the accommodation of the stresses that are incurred, must also insure that the positions of x-ray tubes and detectors is rigidly maintained, since position shifts of the components of more than 0.15 mm can lead to a significant degradation of the image quality.

Significant primary requirements for the rotor of a gantry are accordingly not only a high stability to transfer the forces but also a high rigidity in order to keep deformations of the rotor (and thus the position shifts of the components of the acquisition device) below the allowable limits, given a simultaneously low weight.

An additional thickening of the existing design would be necessary in order to achieve rotation speeds of 300 R/min and more while keeping the same material. The consequence would be a weight increase of the rotor. Components to drive the rotor and the stationary part of the gantry thus would also have to be adapted to the greater weight. This approach has the disadvantage that it leads to a sensitive weight and volume increase of the entire gantry.

SUMMARY OF THE INVENTION

An object of the present invention is to provide a rotor of a gantry of a computer tomography apparatus with a high rigidity and a high stability given a simultaneously low weight of the rotor, such that high rotor rotation speeds can be achieved without negatively affecting the image quality of generated image. An object of the invention is, moreover, to provide a gantry and a computed tomography apparatus with such a rotor.

The rotor according to the invention for a gantry of a computed tomography apparatus is produced (at least in sections) from bar-shaped basic elements in a differential style or mode. The differential style of the rotor is characterized by a low material usage relative to an integral style, and thus by a low total weight of the rotor. Due to the achieved reduction of the weight and of the rotation mass (associated with the weight) that must be accelerated upon rotation of the rotor, higher rotation speeds of the rotor can be achieved with a relatively smaller dimensioning of the drive. Even complex rotor structures can be designed with the differential style by assembly of basic elements of simple design, such that the manufacturing costs are decreased to a significant degree. Spot (point) connections can also be released again in a simple form so that not only the construction but also the dismantling and the recycling of the rotor can be implemented in a simple manner through the existing segmentation of the rotor. The rotor can also be transported in a simpler form due to the weight reduction, which distinctly reduces the transport costs.

In an embodiment of the invention, the basic elements are aligned at least in sections in the direction of force paths arising upon rotation of the rotor, and therefore the forces arising in the rotor and the stresses connected with the forces can be accommodated and relayed in an improved manner.

The basic elements are advantageously mechanically coupled with one another via simply realized spot connections. Rivet connections that can be produced by machine with little effort and with which particularly solid connections can be generated are advantageously used as spot connections. The basic elements at spot connections are advantageously additionally glued to one another. Gluing additionally increases the stability of the connection. Moreover, the adhesive used for gluing can have additional oscillation-damping properties so that vibrations of the rotor are effectively reduced.

For a further efficient material savings, the basic elements has a hollow profile. In an embodiment, a filling material (filler) is inserted into at least some of the basic elements. Additional vibration-damping properties can thereby be realized. A particularly effective damping can be achieved when the filling material is made of aluminum foam.

The basic elements advantageously exhibit an I-profile with a web height, a web thickness and a flange surface that are dimensioned depending on local forces arising upon rotation of the rotor. Due to the I-profile of the basic elements, the rotor possesses a high rigidity and stability, such that deformation of the rotor (and therefore displacement of the scan plane) that degrades the image quality does not occur even at high rotation speeds of the rotor. Due to the planar expansion of the flange surface, it is possible to attach components of the acquisition device to this surface in a particularly simple manner.

A rotor with high rigidity and stability can also be realized with a box profile of the basic elements.

In another embodiment of the invention, the basic elements form a framework structure with a rotor wall and a peripheral retention ring provided on the outer or inner circumference of said rotor wall. This retention ring serves for the mounting of components of an acquisition device. An attachment plate fixed via the basic elements is provided in at least one region of the rotor wall and/or in a region of the retention ring. Components of the acquisition device and/or of the rotation bearing device can be arranged on the attachment plate in a simple manner. Gaps in the framework structure are closed by the additional integration of the attachment plates, such that the stability of the rotor is additionally increased. For example, fastening plates made from a sheet can be produced.

The necessary rigidity and stability of the rotor can be achieved when the basic elements are produced from a steel alloy, a wrought aluminum alloy or a composite material with metal or polymer matrix. Naturally, it would also be possible to produce the basic elements that from different materials from those used to design of the rotor.

DESCRIPTION OF THE PREFERRED EMBODIMENTS

Figure 1:
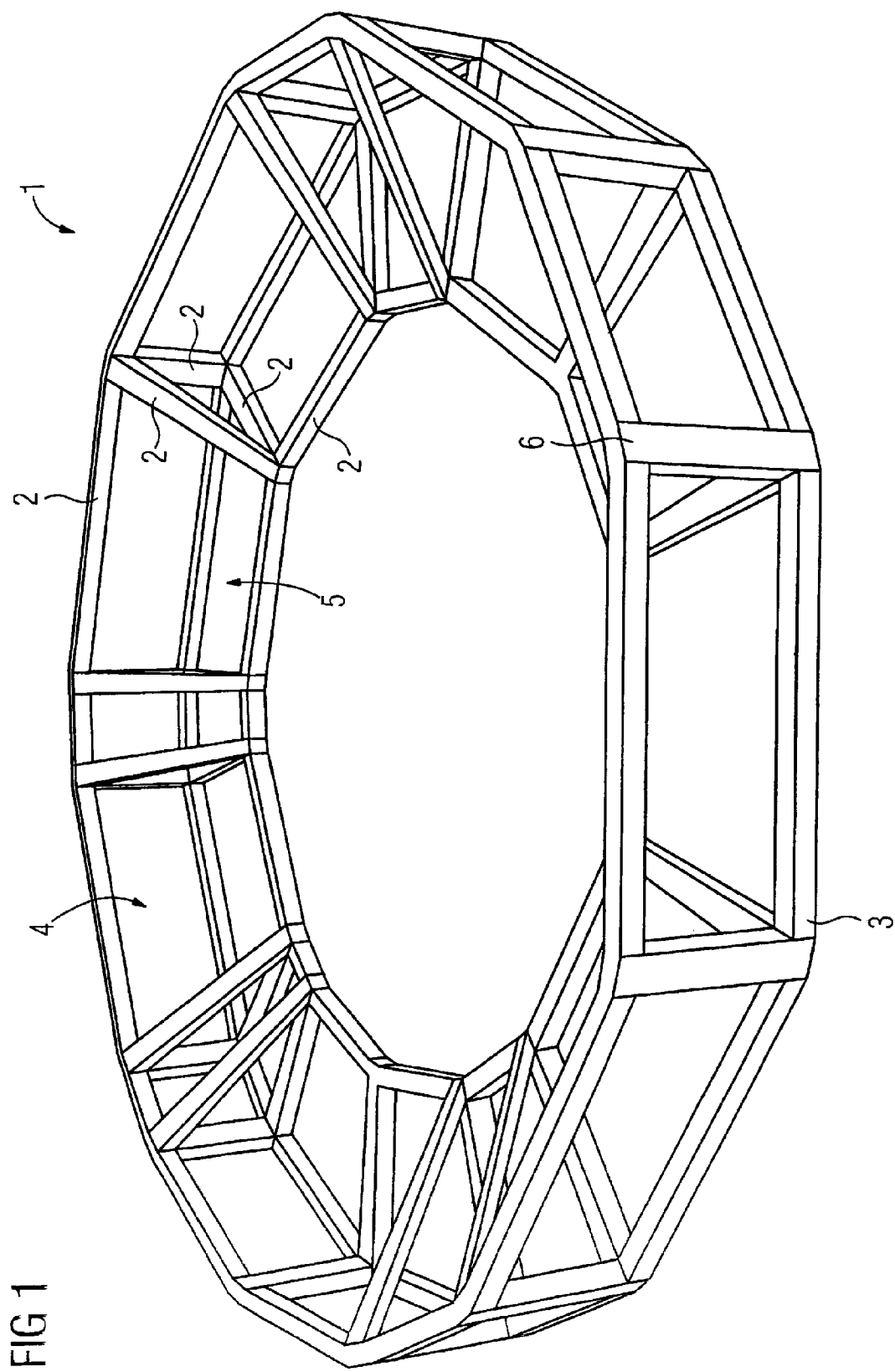
FIG. 1 shows, in perspective view, a rotor according to the invention in a differential style, with a rotor wall and a peripheral retention ring provided on the outer circumference of said rotor wall, which retention ring serves for the mounting of components of an acquisition device.

A rotor 1 according to the invention for a gantry of a computer tomography apparatus is shown in perspective in FIG. 1, which rotor 1 is produced in a differential style from bar-shaped basic elements 2. For clarity, only a few of the basic elements are provided with reference numbers. Due to the framework structure arrangement of the basic elements 2, a significant reduction of the weight or, respectively, of the rotation mass can be produced in comparison to an integral style of the rotor 1. In this way high rotor rotation speeds can be realized while maintaining the rigidity and the stability of the rotor 1 and given comparably smaller dimensioning of a drive.

Due to the framework structure arrangement of the basic elements 2, in this exemplary embodiment a rotor wall 5 in the shape of a ring wheel and a peripheral retention ring 4 provided on the outer circumference of said rotor wall 5 are formed for the mounting of components of an acquisition device of the computed tomography apparatus. The basic elements 2 between the outer and inner contour of the rotor wall 5 run in the radial direction and are thus aligned in the direction of force paths arising upon rotation of the rotor 1. The forces created in the rotor 1 upon rotation are effectively relayed via a rotating bearing device (provided on the inner contour of the rotor wall 5) to the stationary part of the gantry (not shown in this exemplary embodiment) without destabilizing stresses being generated in the rotor 1.

As is apparent from FIG. 1, additional braces formed by basic elements are present between the retention ring 4 and the rotor wall 5, whereby the rigidity of the rotor 1 is additionally increased.

In total only five basic elements 2 of different dimensions are necessary to construct the rotor 1 shown in this exemplary embodiment. The basic elements 2 thereby differ only with regard to their length dimension. Thus only two basic elements 2 of different dimensions are necessary to construct the retention ring 3 and the outer contour of the rotor wall 5. Two additional basic elements 2 with a different dimensioning result from the formed inner contour of the rotor wall 5 and the radial braces running between the inner contour and the outer contour. Moreover, an additional basic element 2 with a different dimensioning relative to these is necessary to produce the brace between retention ring 4 and the rotor wall 5. Very complex rotor structures are thus to be realized with only a few basic elements 2 of different dimensions or shapes.

The basic elements 2 are mechanically coupled with one another via spot connections 3, wherein only one of the connections is provided with a reference character. Spot connections 3 in particular possess the advantage that, on the one hand, very solid connections can be produced, and on the other than that the connections can also be released again in a simple manner for repair, disassembly or recycling purposes. In particular rivets are suitable as a joining technology for the differential components. Rivet connections can be very easily produced by machine. An effective force transfer between the components additionally occurs via the introduced rivets.

In addition to the rivets, the components are advantageously glued to one another. The gluing not only has a stabilizing function but also a vibration-damping function. By selecting the corresponding adhesive which possesses a certain elasticity, it can be brought about that mechanical vibrations between the basic elements 2 are damped due to an acoustic impedance of the adhesive that is used.

Given a connection of basic elements 2 in the longitudinal direction, a simple connection is possible by telescoping the basic elements 2. It is a requirement for this that the inner dimensions of the profile of the first basic elements 2 correspond to the outer dimensions of the profile of the second basic element 2 at the connection point.

By contrast, a node point 6 must be provided at connection points at which multiple basic elements 2 converge. This node point 6 can be executed as a cast part, for example made of cast iron or cast steel. The shape and size of a node point 6 depend on a selected material and the number of profiles that should be connected with one another.

A very efficient material savings is possible when the basic elements 2 exhibit a hollow profile. For additional damping of vibrations it would be conceivable that at least a portion of the hollow profile or a portion of the basic elements 2 has a filling material with vibration-damping properties. A particularly effective damping can be achieved when foamed aluminum is used as a filling material, for example.

The basic element 2 can have very different profiles. The I-profile, which exhibits a web height, a web thickness and a flange surface, is particularly suitable. A rotor that has a high rigidity and solidity can be achieved with such a profile. It is appropriate for web height, web thickness and flange surface to be dimensioned differently depending on local forces arising upon rotation of the rotor 1. In this way it is possible to adapt basic elements 2 to the locally present requirements with regard to the mechanical load. Naturally, other profiles (for example box profiles) of the basic elements 2 can also be selected with which a similarly high rigidity and stability can be achieved.

In principle, the more basic elements 2 or braces that are provided within the framework structure, the more rigid the construction and the more connection points that are needed. The load on the interface simultaneously decreases. A sectional weakening is compensated by the rivet holes. An optimal number of basic elements 2 that are used to produce the rotor is found by selection of a balanced ratio between rigidity and total weight of the rotor. Both arrangement of the basic elements 2 and density of the framework structure can be determined either experimentally or with the aid of numerical models via a simulation.

Components of the acquisition device of the computed tomography apparatus can be directly attached (i.e. bolted) to the basic elements 2. For this purpose, it is normally necessary to reinforce the basic elements 2 at the points of the connection to be established via an addition of material. In particular, a machine processing (for example by the introduction of threads) can be possible via an addition of material. Moreover, it would be conceivable to attach fastening plates between the basic elements 2, on which fastening plates the components of the acquisition device (in particular the x-ray radiator and the x-ray detector) are subsequently mounted. In order to prevent the components from being expelled from the rotor region in the event of failure of the produced connection, the retention ring can be additionally closed with additional fastening plates that moreover also increase the rigidity of the overall structure. Such fastening plates can be sheets, for example, that are riveted with the basic elements 2.

Wrought aluminum alloys or steel alloys that have a high stability and rigidity as construction material can be used to produce the basic elements 2. However, it would also be conceivable to produce the basic elements 2 from composite materials. Composite materials with both metal and polymer matrix are suitable. Fibers or particles are considered as reinforcement material, or even a mixture of the two. The rotor 1 can be built from basic elements 2 that are produced form different materials.

Figure 2:
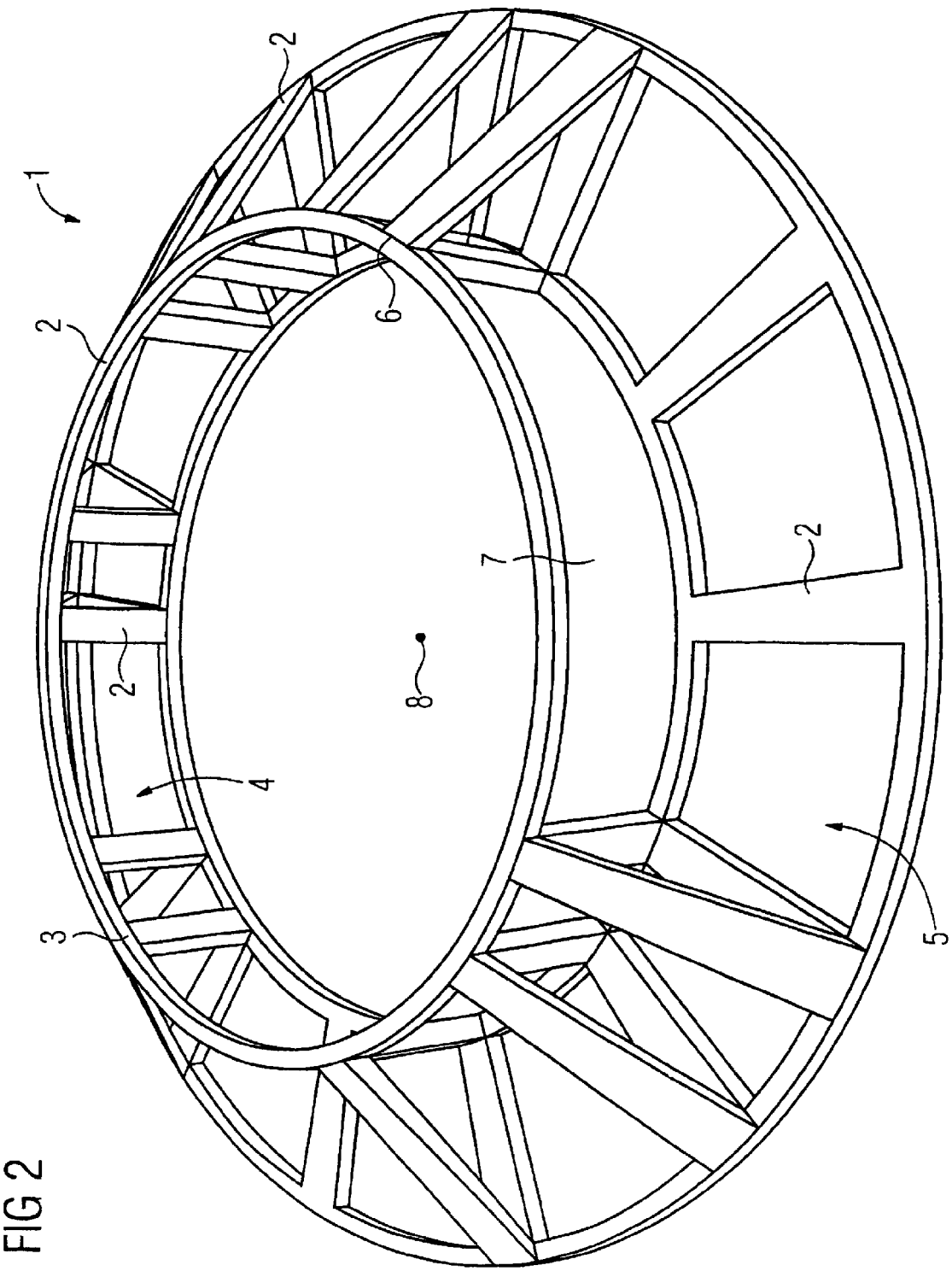
FIG. 2 shows, in perspective view, a rotor according to the invention in a differential style in a second exemplary embodiment, with—in contrast to FIG. 1—a peripheral retention ring provided on the inner circumference of the rotor wall.

A rotor 1 according to the invention in a differential style is shown with a perspective view in FIG. 2 in a second exemplary embodiment. In contrast to FIG. 1, the retention ring 4 is not arranged on the outer circumference of the rotor wall 5 but rather on the inner circumference of said rotor wall 5. A greater component rigidity can be achieved with this basic design of the rotor structure. The reason for this is the shorter force flow runs within the rotor 1. Via the retention ring 4 arranged on the inner ring, a portion of the centrifugal forces near the bearing are introduced into the rotation bearing device. Ideally, the components of the acquisition device are arranged centered in relation to the rotation bearing device (likewise arranged on the retention ring 4). The rotor wall 5 is additionally available for bolting the components. The structure can also take on a reinforcing function for the components.

The basic elements 2 on the retention ring 4 can be arranged so that a recess 7 is formed for at least one of the components of the acquisition device, which recess 7 is dimensioned such that the component can be inserted in a radial direction traveling away from a rotation center 8 of the rotor 1 and can be positively connected with the rotor via a stop provided at the component. In this way it can be prevented that the component is expelled out of the rotor region upon failure of a bolt connection for retention of the component.

In summary, the invention concerns a computed tomography apparatus and a rotor 1 for a computer tomography apparatus, wherein the rotor 1 is produced at least in sections in a differential style from bar-shaped basic elements 2. Due to the differential style of the rotor 1, the rotation mass is reduced to a significant degree given a simultaneously maintained rigidity and stability of the rotor 1, such that high rotation speeds can be realized with a comparably small dimensioning of the rotor drive.

Although modifications and changes may be suggested by those skilled in the art, it is the intention of the inventors to embody within the patent warranted hereon all changes and modifications as reasonably and properly come within the scope of their contribution to the art.

We claim as our invention:

1. A rotor for a gantry of a computed tomography apparatus comprising:
    a rotor structure consisting of a plurality of bar-shaped basic elements connected rigidly together in a differential style configuration;
    said rotor structure having a size and shape designed to support components of computed tomography gantry; and
    said bar-shaped basic elements having a total combined mass and being connected with rigidity in order to cause said rotor structure to be structurally intact at a rotation speed of said gantry of at least 300 rotations per minute.

2. A rotor as claimed in claim 1 wherein said basic elements are aligned in said differential style configuration, at least in sections, in respective directions of force paths that occur upon rotation of said rotor.

3. A rotor as claimed in claim 1 wherein said basic elements are connected to each other in said differential style configuration by spot connections.

4. A rotor as claimed in claim 3 wherein said spot connections are rivet connections.

5. A rotor as claimed in claim 3 wherein said basic elements are glued to each other at said spot connections.

6. A rotor as claimed in claim 1 wherein each of said basic elements has a hollow profile.

7. A rotor as claimed in claim 6 comprising a filling material having vibration-damping properties that fills said hollow profile.

8. A rotor as claimed in claim 7 wherein said filling material is aluminum foam.

9. A rotor as claimed in claim 1 wherein each of said basic elements has an I-profile with a web height, a web thickness and a flange surface dimensioned dependent on local forces that arise upon rotation of said rotor.

10. A rotor as claimed in claim 1 wherein said basic elements each exhibit a box profile.

11. A rotor as claimed in claim 1 wherein said basic elements form a framework structure with a rotor wall and a peripheral retention ring at an outer or inner circumference of said rotor wall, said retention ring being configured to mount said components.

12. A rotor as claimed in claim 11 comprising at least one attachment plate attached to said basic elements in a region of said outer wall or a region of said retention ring.

13. A rotor as claimed in claim 1 wherein at least some of said basic elements are comprised of a steel alloy.

14. A rotor as claimed in claim 1 wherein at least some of said basic elements are comprised of a wrought aluminum alloy.

15. A rotor as claimed in claim 1 wherein at least some of said basic elements are comprised of a composite material having a metal matrix.

16. A rotor as claimed in claim 1 wherein at least some of said basic elements are comprised of a composite material having a polymer matrix.

17. A computed tomography apparatus comprising:
    a stationary frame;
    a gantry mounted for rotation in said stationary frame; and
    a rotor structure inside said gantry, said rotor structure consisting of, at least in sections, a plurality of bar-shaped basic elements connected together in a differential style configuration; and
    said bar-shaped basic elements having a total combined mass and being connected with rigidity in order to cause said rotor structure to be structurally intact at a rotation speed of said gantry of at least 300 rotations per minute.

* * * * *